(12) United States Patent
Muhsin et al.

(10) Patent No.: US 9,877,650 B2
(45) Date of Patent: Jan. 30, 2018

(54) PHYSIOLOGICAL MONITOR WITH MOBILE COMPUTING DEVICE CONNECTIVITY

(71) Applicant: MASIMO CORPORATION, Irvine, CA (US)

(72) Inventors: Bilal Muhsin, Aliso Viejo, CA (US); Sujin Hwang, Rancho Santa Margarita, CA (US); Benjamin C. Triman, Rancho Santa Margarita, CA (US)

(73) Assignee: MASIMO CORPORATION, Irvine, CA (US)

( * ) Notice: Subject to any disclaimer, the term of this patent is extended or adjusted under 35 U.S.C. 154(b) by 125 days.

(21) Appl. No.: 14/033,315

(22) Filed: Sep. 20, 2013

(65) Prior Publication Data

US 2014/0081100 A1 Mar. 20, 2014

Related U.S. Application Data

(60) Provisional application No. 61/703,729, filed on Sep. 20, 2012.

(51) Int. Cl.
| | | |
|---|---|---|
| *A61B 5/1455* | (2006.01) | |
| *A61B 5/00* | (2006.01) | |
| *A61B 5/0476* | (2006.01) | |
| *A61B 5/0402* | (2006.01) | |
| *A61B 5/0205* | (2006.01) | |
| *A61B 7/00* | (2006.01) | |

(52) U.S. Cl.
CPC ........ *A61B 5/0002* (2013.01); *A61B 5/02055* (2013.01); *A61B 5/0402* (2013.01); *A61B 5/0476* (2013.01); *A61B 5/14551* (2013.01); *A61B 5/7203* (2013.01); *A61B 5/7225* (2013.01); *A61B 5/742* (2013.01); *A61B 7/003* (2013.01); *A61B 2562/22* (2013.01)

(58) Field of Classification Search
CPC .............. A61B 5/4818; A61B 5/14551; A61B 5/02416; A61B 5/14552; A61B 5/7207
See application file for complete search history.

(56) References Cited

U.S. PATENT DOCUMENTS

| | | | | |
|---|---|---|---|---|
| 5,692,505 | A * | 12/1997 | Fouts ........................... 600/336 |
| 2006/0224059 | A1 * | 10/2006 | Swedlow et al. ............. 600/323 |
| 2008/0071153 | A1 * | 3/2008 | Al-Ali ................ A61B 5/14552 600/310 |
| 2008/0211657 | A1 * | 9/2008 | Otto .............................. 340/501 |
| 2010/0198094 | A1 * | 8/2010 | Turicchia et al. ............ 600/528 |
| 2011/0071370 | A1 * | 3/2011 | Al-Ali ........................... 600/301 |
| 2011/0077473 | A1 * | 3/2011 | Lisogurski ................... 600/301 |
| 2011/0209915 | A1 * | 9/2011 | Telfort ............... A61B 5/04282 174/71 R |

* cited by examiner

*Primary Examiner* — Eric Winakur
*Assistant Examiner* — Marjan Fardanesh
(74) *Attorney, Agent, or Firm* — Knobbe, Martens, Olson & Bear LLP

(57) ABSTRACT

Systems and method for monitoring patient physiological data are presented herein. In one embodiment, a physiological sensor and a mobile computing device can be connected via a cable or cables, and a processing board can be connected between the sensor and the mobile computing device to conduct advanced signal processing on the data received from the sensor before the data is transmitted for display on the mobile computing device.

21 Claims, 15 Drawing Sheets

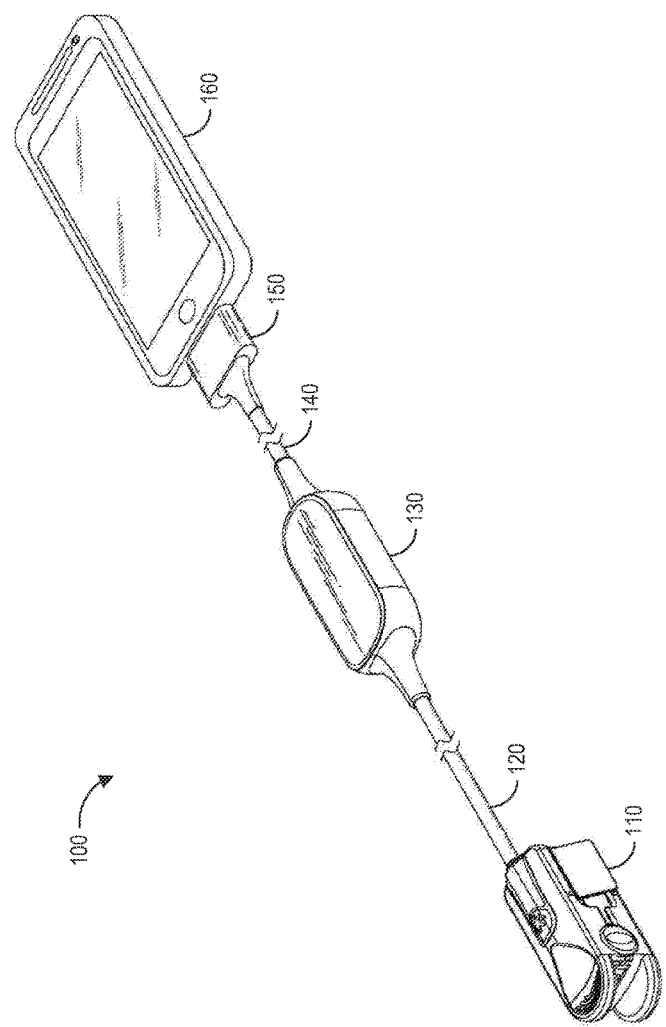

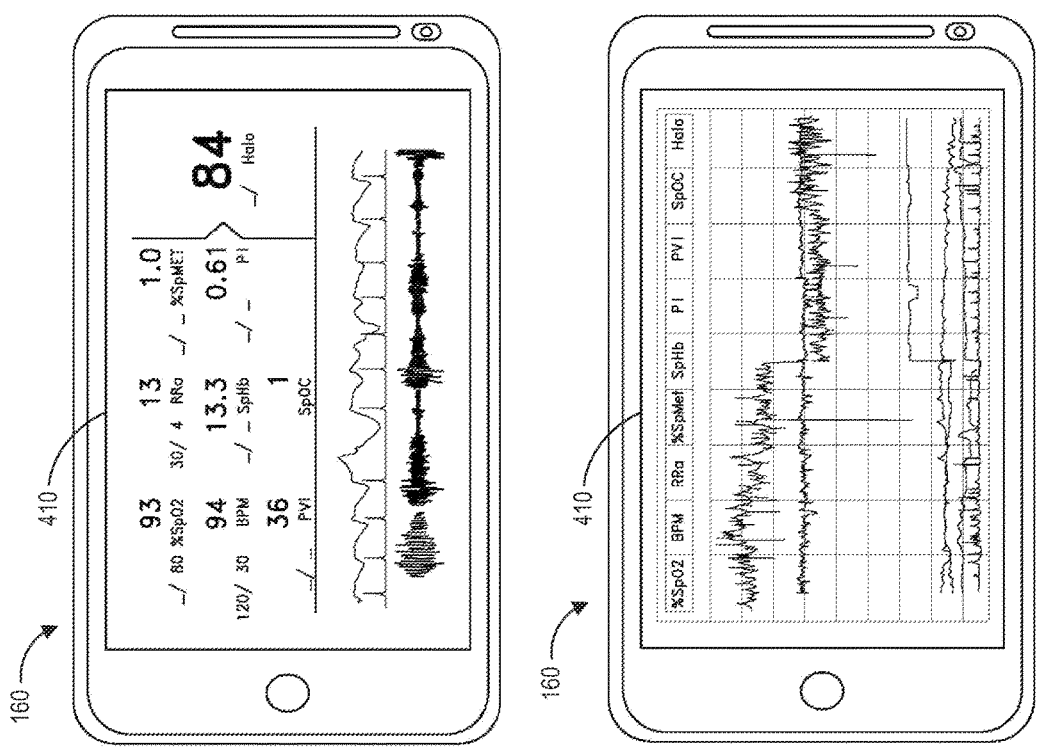

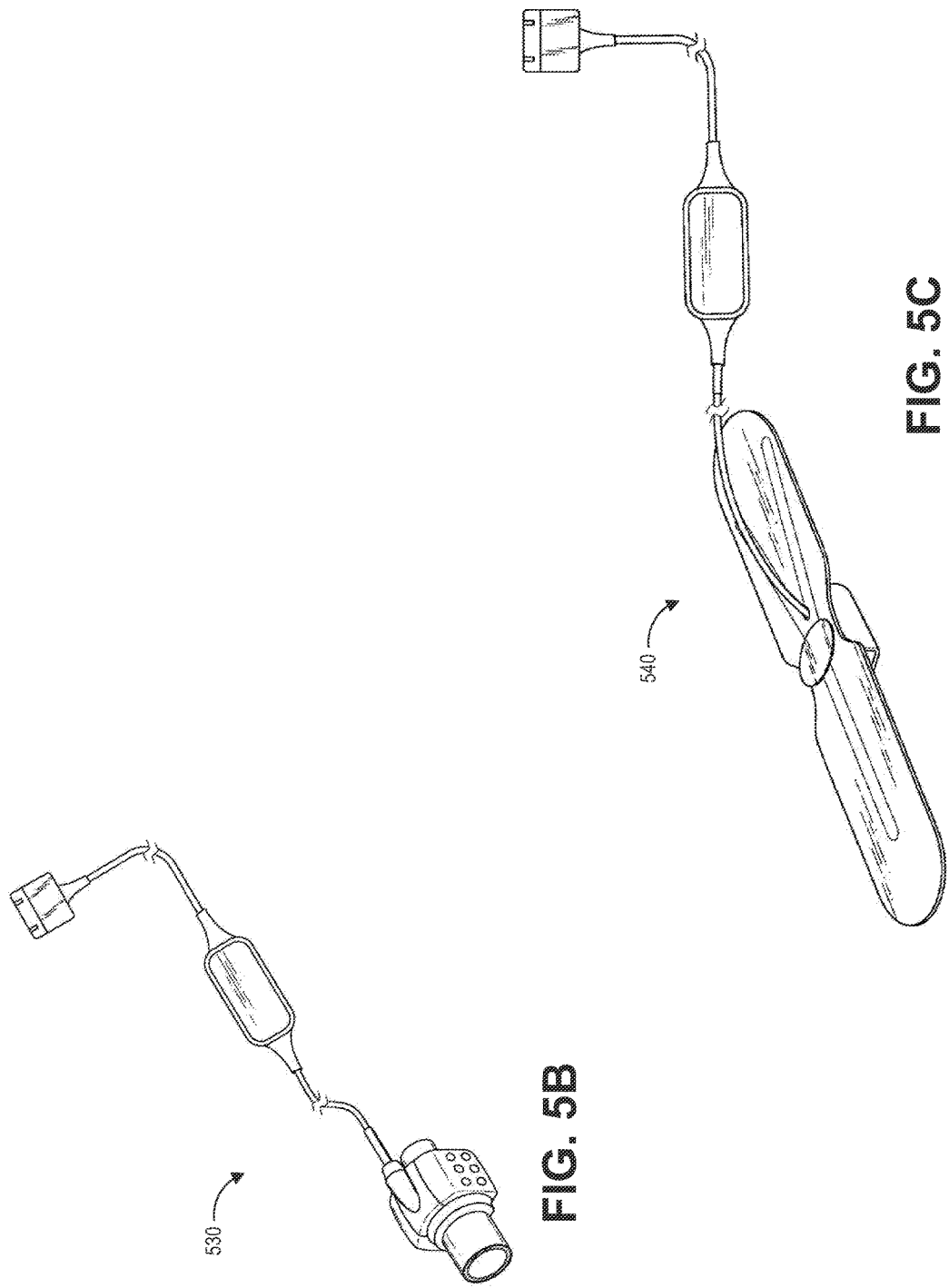

PHYSIOLOGICAL MONITOR WITH MOBILE COMPUTING DEVICE CONNECTIVITY

RELATED APPLICATIONS

This application claims the benefit of U.S. Provisional Application No. 61/703,729 filed Sep. 20, 2012, entitled "Patient Monitor with Mobile Computing Device Connectivity," the disclosure of which is hereby incorporated by reference in its entirety.

BACKGROUND

Field of the Disclosure

The present disclosure relates in general to noninvasive patient monitoring systems, including oximeters and co-oximeters, and their accessories such as sensors or cables. In particular, this disclosure relates to patient monitors capable of connectivity to a mobile computing device.

Description of the Related Art

Oximetry utilizes a noninvasive optical sensor to measure physiological parameters of a patient. In general, the sensor has light emitting diodes (LEDs) that transmit optical radiation into a tissue site and a detector that responds to the intensity of the optical radiation after absorption (e.g., by transmission or transreflectance) by, for example, pulsatile arterial blood flowing within the tissue site. Based on this response, a processor determines measurements for oxygen saturation ($SpO_2$), pulse rate, plethysmograph waveforms, perfusion quality index (e.g., an index that quantifies perfusion), assessments of other blood constituents, parameters or analytes, including for example, a percent value for arterial carbon monoxide saturation (HbCO), a percent value for methemoglobin saturation (a brownish-red form of hemoglobin that cannot function as an oxygen carrier) (HbMet), total hemoglobin (HbT), fractional $SpO_2$ ($SpaO_2$) or the like. Additionally, caregivers often desire knowledge of $HbO_2$, Hb, blood glucose (HbGu), water, the presence or absence of therapeutic drugs (aspirin, Dapson, nitrates, or the like) or abusive/recreational drugs (methamphetamine, alcohol, steroids, or the like), concentrations of carbon dioxide ($CO_2$), oxygen ($O_2$), oxygen concentration, pH levels, bilirubin, perfusion quality, albumin, cyanmethemoglobin, and sulfhemoglobin (HbSulf), signal quality or the like. It is noted that "oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood.

Oximeters capable of reading many of the foregoing parameters during noise due to patient movement, electromagnetic interference, and ambient light are available from Masimo Corporation (Masimo) of Irvine, Calif. Moreover, portable and other oximeters are disclosed in at least U.S. Pat. Nos. 6,770,028, 6,658,276, 6,157,850, 6,002,952, and 5,769,785, incorporated by reference herein, and others patent publications such as those listed at http://www.masimo.com/patents.htm. Such noise filtering oximeters have gained rapid acceptance in a wide variety of medical applications, including surgical wards, intensive care and neonatal units, general wards, home care, physical training, and virtually all types of monitoring scenarios. Some blood parameter monitors including oximeters are the standard of care in certain critical environments like surgery and neonatal care.

SUMMARY

Mobility and ease of use are key factors in the health care industry because they correlate to efficient, rapid patient care as well as enable patients to participate in their own care. Therefore, the present disclosure provides physiological monitoring devices which are compatible with handheld monitors such as common mobile computing devices for ease of use and portability.

This disclosure describes embodiments of a mobile physiological sensor that can be conveniently used in conjunction with existing mobile devices of users in a variety of contexts. In certain embodiments, a physiological monitoring system can be designed to include a sensor and cable assembly with a processing board or card, and the system can be connectable to a mobile computing device, such as a smartphone, such that display of the monitored physiological data can occur on the computing device. The board or card can communicate the data for display with the mobile computing device wirelessly or through a physical and electrical connection with the cable assembly. In some embodiments, the board or card can include one or more signal processors and associated memory, I/O, and the like to provide monitored physiological data to applications executing on traditional smartphone processing environments, such that board or card handles advanced signal processing and the smartphone displays parameter data. In an embodiment, the board is housed in a portion of the cable such that it is not directly coupled to the sensor or the smartphone connector. This configuration has the advantage of mechanically isolating the board so that it does not encumber the sensor or the smart phone connection. As a result, the physiological monitoring system can be more portable than existing monitoring systems, thereby facilitating enhanced patient care for more patients.

For example, such a system can be sent home with a patient to gather physiological measurement data outside the hospital setting. In addition, portable physiological monitoring equipment as disclosed herein can facilitate the gathering of physiological measurement data in a variety of other contexts, such as sports or extreme sports, military training and combat, aviation, health awareness, high-altitude activities, monitoring of professionals in dangerous conditions, screening for medical conditions such as congenital heart defects, field hospitals, and mobile medical clinics, to name a few.

Physiological monitoring systems such as those that are described herein enable oximeter use outside of the traditional hospital setting. This is beneficial for more comprehensive patient care. For instance, prior to a surgical procedure during which a patient will be sedated, such as by general anesthesia, a physician can be concerned about the patient's proclivity toward apnea. A portable oximetry sensor compatible with the patient's smartphone can be sent home with the patient prior to the procedure, and the sensor can be worn overnight. Data collected from the sensor can be passed to the smartphone and made available to the doctor, such as by uploading to the internet or being downloadable from the device, to identify a risk of hypoxemia. This example illustrates one of the many benefits of a portable oximetry system compatible with a common mobile computing device.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIG. 1A illustrates an embodiment of a physiological monitoring system.

FIGS. 4A-4D illustrate various embodiments of software applications for display and management of physiological monitoring data.

FIGS. 5A-5C illustrate various embodiments of mobile physiological sensors assemblies.

DETAILED DESCRIPTION

I. Example Mobile Physiological Monitoring Systems

Figure 1B:
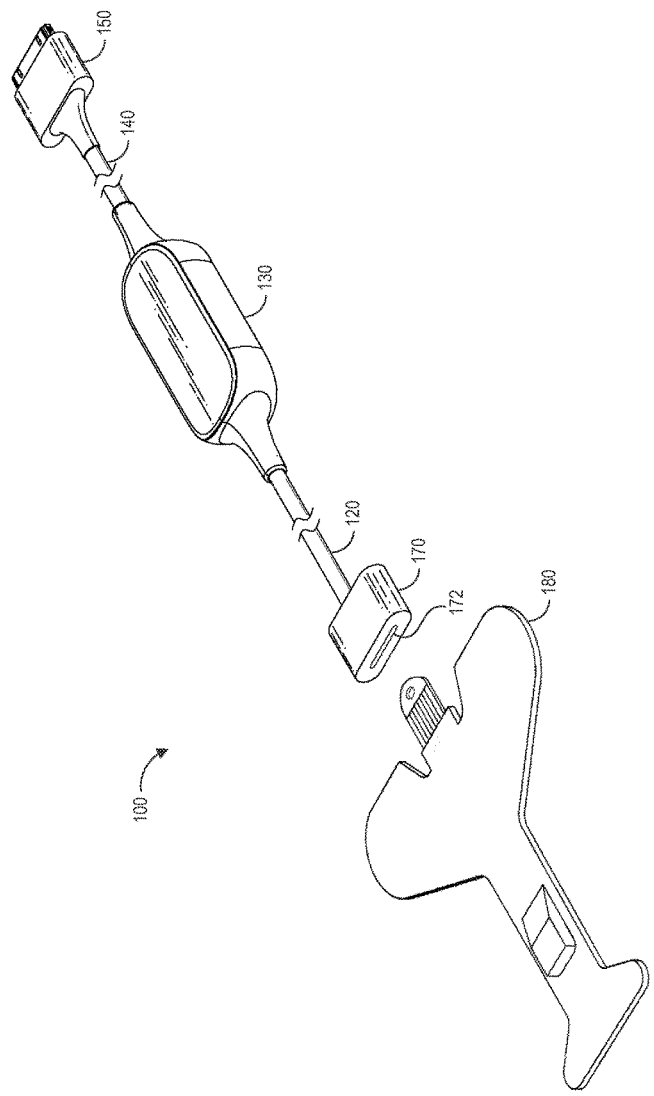
FIG. 1B illustrates another embodiment of a physiological monitoring system.
Figure 1C:
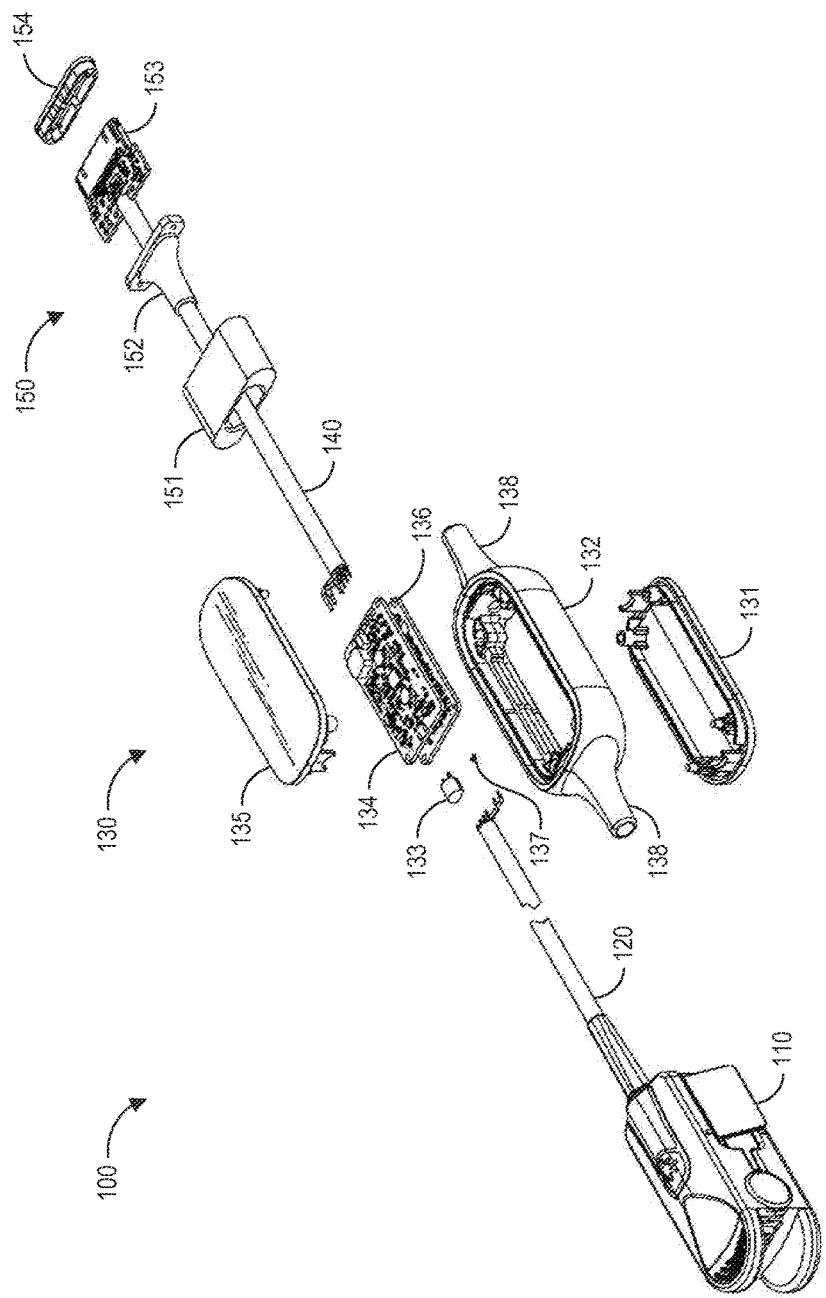
FIG. 1C illustrates an exploded view of one embodiment of the cable components of FIG. 1A.

FIGS. 1A, 1B, and 1C illustrate embodiments of a physiological monitoring system 100. The physiological monitoring system 100 shown in FIG. 1A includes a sensor 110, first cable 120, processing module 130, second cable 140, connection port 150, and a mobile computing device, illustrated here as smartphone 160. Although specific reference can be made to smartphones in this disclosure, any mobile computing device compatible with the physiological sensor system can be used. A compatible mobile computing device can be one of a wide range of mobile devices such as a mobile communications device (such as a smartphone), laptop, tablet computer, netbook, PDA, media player, mobile game console, wristwatch, wearable computing device, or other microprocessor based device configured to interface with a physiological sensor. Some embodiments of the mobile computing device can be used with the system for display of data and/or storage of data. Cables 120, 140 used with the device can be flex cables or other cables, including cables having triboelectric properties.

As illustrated, the sensor 110 can be a pulse oximeter capable of being secured to a digit such as a finger, for example the Masimo Rainbow® pulse oximeter. However, this is for illustrative purposes only, and the sensor 110 can be any physiological sensor. In some embodiments, other varieties of pulse oximeters can be used, for example adhesive sensors, combination reusable/disposable sensors, soft and/or flexible wrap sensors, infant or pediatric sensors, multisite sensors, or sensors shaped for measurement at a tissue site such as an ear. In other embodiments, the sensor 110 can be any of a variety of sensors, such as a pulse oximeter, a brain function monitor such as an electroencephalograph ("EEG"), a gas monitor such as a capnometer or capnograph, an acoustic respiratory sensor, a heart function monitor such as an electrocardiograph ("ECG"), blood alcohol level sensors, temperature sensors, respiratory inductive plethysmography bands, bioelectric sensors, electronic fetal monitors, or the like. The sensor 110 can be reusable in some embodiments, can be disposable in some embodiments, and in other embodiments the sensor 110 can have both reusable and disposable components. In some embodiments, the sensor can be available in different sizes.

As illustrated in FIG. 1B, in an embodiment, cable 120 can include a port 170 at the sensor-facing end of the cable 120, and a disposable, connectable sensor 180 may be attached to the cable 120. In some embodiments, the connectable sensor 180 can be reusable, or can be partially reusable and partially disposable. A sensor connection mechanism 172 can be configured to receive, or otherwise connect to, connectable sensors of different types, such as any of the physiological sensors discussed above. Although connection port 150 is illustrated as being configured for physical and electrical connection to a mobile device, in some embodiments, the connection port may be a wireless connection port configured to wirelessly transmit filtered physiological parameter data to the mobile device or another computing device.

In various oximeter embodiments, the sensor 110 provides data in the form of an output signal indicative of an amount of attenuation of predetermined wavelengths (ranges of wavelengths) of light by body tissues, such as, for example, a digit, portions of the nose or ear, a foot, or the like. The predetermined wavelengths often correspond to specific physiological parameter data desired, including for example, blood oxygen information such as oxygen content ("SpOC"), oxygen saturation ("SpO2"), blood glucose, total hemoglobin ("SbHb"), methemoglobin (SbMet"), carboxyhemoglobin ("SpCO"), bulk tissue property measurements, water content, pH, blood pressure, respiration related information, cardiac information, indications of perfusion ("PI"), pleth variability indices ("PVI"), or the like. In some embodiments, sensor data can provide information regarding physiological parameters such as EEG, ECG, acoustic respiration rate ("RRa"), end-tidal carbon dioxide ("EtCO$_2$"), return of spontaneous circulation ("ROSC"), or the like.

The sensor data can be corrupted by noise due to patient movement, electromagnetic interference, or ambient light. Therefore, the sensor data is transmitted from sensor 110 along the first cable 120 to the processing module 130, which can apply noise filtering and signal processing techniques described below to provide output data for display on the smartphone 160. Such complex processing techniques can exceed the processing capabilities of the smartphone 160, and therefore the processing module 130 drives operation of the sensor 110 and handles signal processing and transmits the processed sensor parameter data as output measurement data. Smartphone 160 can be coupled to the processing module 130 by a second cable 140 and connection port 150, in some embodiments, and in other embodiments can be configured to wirelessly transmit the parameter data to the smartphone 160 or another computing device.

Smartphone 160 can include a display screen such as an LED or LCD screen, and can include touch sensitive technologies in combination with the display screen. Smartphone 160 can include software configured to display some or all of the output measurement data on the display screen. The data display can include numerical or graphical representations of blood oxygen saturation, heart rate, and/or a plethysmographic waveform, and some embodiments can simultaneously display numerical and graphical data representations.

The smartphone 160 can include software such as an application configured to manage output measurement data from the processing module 130. The application functionality can include trend analysis, current measurement information, alarms associated with above/below threshold readings, reminders to take measurement data at certain times or cycles, display customization, iconic data such as hearts beating, color coordination, bar graphs, gas bars, charts, graphs, or the like, all usable by a caregiver or smartphone user to enable helpful and directed medical monitoring of specified physiological parameters. The smartphone 160 can also include network connection capabilities such as one or more of a cellular network, satellite network, Bluetooth, ZigBee, wireless network connection such as Wi-Fi, and a wired network connection.

In some embodiments, software capable of analyzing the output measurement data received from the processing module 130 and making the data available in an appropriate manner for health management is installed on the smartphone 160. In some embodiments, the smartphone 160 includes software which allows a user to view the data in a multitude of ways. For example, in some embodiments a user can be able to view the raw data received from the sensor 110. In other embodiments, a user can be able to select from a plurality of graphical representations of the data (e.g., bar graphs, charts, etc). In other embodiments, the user can be able to manipulate the data to visualize trends in the data. The smartphone 160 can also be able to alert the user and/or a physician or other care provider to an abnormal data reading. For example, an abnormally low or high blood oxygen saturation reading can cause the smartphone 160 to buzz, vibrate or otherwise notify the user of an abnormal reading, or to transmit a notification to a physician via a network.

The smartphone 160 can have the capability of sending physiological data to a computer (e.g., a home computer) on which the user manages his health data. The data can also be sent to a physician or pharmacist for their expertise and feedback. The smartphone 160 and the computing device to which data is being sent can be connected directly or via a network such as a LAN, WAN or the Internet. The connection can be wired or wireless. Other connection configurations are also possible.

The system 100 as illustrated in FIG. 1C shows an exploded view of the processing module 130 and the connection port 150 to reveal the components thereof. The processing module 130 drives operation of the sensor 110 and receives raw detected signals from the sensor 110. The processing module 130 processes the raw detected signals to determine a physiological measurement. The processing module 130, in some embodiments, employs advanced signal processing techniques, including parallel engines and adaptive filters, to allow accurate monitoring of arterial oxygen saturation and pulse rate even during the most challenging conditions. In some embodiments, the processing module 130 can employ Signal Extraction Technology, or Masimo SET®, using parallel signal processing engines to separate the arterial signal from sources of noise (including the venous signal) to measure $SpO_2$ and pulse rate accurately, even during motion. The processing module 130 can filter raw physiological sensor data input from the sensor 110, and the processing module 130 can provide filtered physiological parameter data to the mobile computing device for display or storage.

One drawback of implementing physiological measurement technology on mobile computing devices is the processing overhead typically required for recognizing parameters from data input by the sensor by filtering such raw physiological measurement data. Processing overhead measures the total amount of work the central processing unit (CPU) of the device can perform and the percentage of that total capacity which is used by individual computing tasks, such as filtering raw physiological measurement data. In total, these tasks must require less than the processor's overall capacity. Moreover, complicated software required to process raw signals and determine physiological measurements can be stored in the processing module 130 in a separate memory unit separate from the mobile device. This frees up memory available to the mobile device.

The current generation of mobile processors is not well adapted to deal with the complexity and corresponding processing overhead of filtering raw physiological measurement data, especially in conjunction with the many other common high performance uses of mobile devices. As an example, the mobile device processor may be used to run a mobile physiological monitoring application concurrently with receiving sensor data, among other applications selected by the user. Many common mobile applications such as maps, games, email clients, web browsers, etc., are typically open on a user's smartphone. During physiological monitoring, a substantially constant stream of data can be sent from the sensor to the mobile device. Accordingly, if the mobile CPU is required to filter the raw data, device performance can be impaired and the user can experience significant latency in the use of other applications. If the data filtering overhead exceeds the overall processing capacity of the CPU then the mobile device would be incapable of processing the data, and the user can experience serious technical problems as a result.

Overload of the CPU can significantly increase system power consumption. To mitigate the possibility of CPU overload, a larger processor can be provided. However, increasing the size of the mobile processor core or cache would deliver performance increases only up to a certain level, beyond which heat dissipation issues would make any further increase in core and cache size impractical. Additionally, overall processing capacity is further limited by the smaller size of many mobile devices, which limits the number of processors that can be included in the device. Because mobile computing devices are generally battery-powered, high performance uses also shortens battery life.

By providing a separate processing module 130 to mediate the data flow from the sensor 110 to the mobile device 160, the complex signal processing required for generating recognizable physiological parameters from raw sensor data can be handled by the processing module 130 and not the mobile CPU. Moving the signal processing calculations away from the mobile CPU frees it up for important core tasks as well as processing of mobile applications. Further, optimizing the mobile CPU can directly correlate with increased battery life, even considering the power draw of the processing module 130 on the mobile device battery. Accordingly, incorporation of a processing module 130 into a mobile sensor cable can be beneficial for conserving processing of the mobile CPU and for reducing battery demands across the system 100.

Coupled to cable 120 is an information element 133. The information element 133 could be provided through an active circuit such as a transistor network, memory chip, EEPROM (electronically erasable programmable read-only memory), EPROM (erasable programmable read-only memory), or other identification device, such as multi-contact single wire memory devices or other devices, or the like.

The processing module 130 includes a lower shell 131, an enclosure with bend relief 132, processing board 134, and an upper shell 135. The enclosure 132, upper shell 135, and lower shell 131 surround the processing board 134 and can protect the sensitive circuitry of the board 134 from damage. In such an embodiment, processing board 134 is the portion of the module 130 that communicates with the first cable 120 and sensor 110, as well as with the second cable 140 and mobile computing device. In an embodiment, the board 134 can access information stored on the information element 133 of the first cable 120.

In an embodiment, the processing module 130 is located in a middle portion of the cable, away from either the sensor 110 or the connection port 150. The processing module 130 can be located a first distance from, and mechanically isolated from, the sensor, so as not to interfere with the placement of the sensor on a measurement site of a user's body. This placement prevents the sensor from being encumbered by the processing module 130 and interfering with placement and use of the sensor. Thus, the sensor is also kept relatively lightweight for ease of use. The processing module 130 can be located a first distance from, and mechanically isolated from, the connection port 150, so as not to interfere with the ability of the connection port 150 to secure to a user's mobile device. This allows the connection port 150 to be unencumbered by the bulk and weight of the processing module 130 which could interfere with the connection to the user's mobile device. In some embodiments, the second distance can be smaller than the first distance, placing the processing module 130 closer to the connection port 150 than to the sensor 110. This prevents the weight of the processing module 130 from interfering with or pulling on the sensor 110. In an embodiment, the components of the processing module 130 are constructed from lightweight materials in order to avoid pulling the sensor 110 off of a user or disconnecting the connection port 150 from a mobile device.

The processing module 130 and sensor 110 draw power for operation from the mobile computing device for operation. This frees the processing module 130 from needing a separate power source. Also, although a display screen can be included on the processing module 130, no separate display screen is necessary as the measurements are displayed on the user's mobile device.

The enclosure 132 can have a bend relief portion 138 on either side. The bend relief portions 138 may enhance the electrical and mechanical integrity and overall performance of the cable assembly by providing a gradual transition from the flexible cables to substantially rigid connection points with the processing board 134 contained within the enclosure. The bend relief portions 138 can prevent mechanical force, such as an axial load or flexing, that is applied to the exterior of either cable 120, 140 from being transferred to the electrical terminations with the processing board 134. The bend relief portions 138 can be premolded and formed with the body of the enclosure, and in some embodiments a crimp ring may be secured around the cable within each bend relief.

The enclosure 132 can be formed, in some embodiments, by a flexible plastic or rubber material. Suitable materials can include thermoplastic rubbers such as Santoprene®. The upper and lower shells 135, 131 can be formed from a hard plastic material. Suitable materials can include thermoplastic polymers. For example, in an embodiment the upper and lower shells 135, 131 can be formed from a blend of two or more of polycarbonate (PC), polyethylene terephthalate (PET), polybutylene terephthalate (PBT), or another polyester, such as Bayer Makroblend® UT5207. In another embodiment, the upper and lower shells 135, 131 can be formed from a resin, for example a blend of semi-crystalline polyester (typically PET or PBT) and PC, such as XENOY™ Resin 6620U. The material for the upper and lower shells 135, 131 can be selected for having desirable impact resistance, toughness, and heat resistance. The upper and lower shells 135, 131 can be formed from the same or different materials.

The body portion of the enclosure 132 can be formed as a gasket which can seal between the upper shell 135 and lower shell 131 and form a substantially water-tight seal, in order to protect the processing board 134 from moisture. In some embodiments, the upper and lower shells 135, 131 can be formed to fit together with the enclosure 132 in a substantially water-tight manner. In an embodiment, the upper and lower shells 135, 131 can be sealed to the enclosure 132 using epoxy around the perimeter of each shell, and/or on mounting posts located on the shell or the enclosure. In some embodiments, the cable entry areas of each bend relief portion 138 of the enclosure 132 can also be filled with epoxy to form a substantially sealed enclosure for the processing board 134.

The cables 120, 140 can be constructed with a Kevlar fiber core for strength and durability, in some embodiments. The Kevlar fiber core can be bundled in the center of a plurality of signal lines, for example five signal lines. The signal lines can be tinned copper jacketed with polypropylene (PP). The bundle of signal lines can be encased in a braided outer shield, for example a tinned copper outer shield with approximately 95% minimum coverage of the bundled signal lines. The outer shield may be encased, in turn, by a multi-layer Teflon film or wrap, in some embodiments, to form a low-friction separator and barrier from an outer jacket. The cables 120, 140 can be further protected by a medical grade PVC outer jacket, or an outer jacket constructed from another biocompatible, flexible plastic or rubber material. Other configurations for the cables 120, 140 are possible. The cables can be designed to have a minimum pull strength of 75 kg, or approximately 75 kg, in some embodiments.

As illustrated, some embodiments can optionally include a second processing board 136. For example, the first processing board 134 can be a digital processing board and the second processing board 136 can be an analog processing board. The analog and digital processing boards may perform separate processing functions. In some embodiments, wires from the first cable 120 can be connected to the analog processing board 136, and wires from the second cable 140 can be connected to the digital processing board 136. In some embodiments, the digital processing board can be in communication with the first information element 133. The first information element 133 can be an EPROM or EEPROM device. The analog processing board can be in communication with a second information element 137 coupled to cable 120. The second information element 127 can be a resistor, in some embodiments, for example an ArCal or ProCal resistor. A resistance value of the resistor can be indicative of a wavelength of light used in an oximetry sensor 110 coupled to the cable 120, and the resistor can be coupled in parallel with the sensor.

In one embodiment, the processing board or boards can include one of many OEM boards commercially available from Masimo which process incoming intensity signals responsive to an amount of attenuation of light in pulsing patient blood and which determine output measurements for a wide variety of physiological parameters from the processing. The processing board 134 can include the MS-2040 OEM board available from Masimo, which can measure Masimo optical SET measurements such as oxygen saturation ($SpO_2$), pulse rate, perfusion index (PI), signal quality (SIQ), optionally pleth variability index (PVI), and the like. The physiological monitoring system 100 can also include, in addition to or instead of the MS-2040 OEM board, other processing boards available from Masimo. For example, the physiological monitoring system 100 can include the MX-5 board available from Masimo, which has variable power consumption based on which parameters are being acquired and displayed. The MX-5 board can measure the Masimo SET parameters described above plus optional Rainbow® parameters including: hemoglobin (SpHb), oxygen content (SpOC), carboxyhemoglobin (SpCO), methemoglobin (SpMet), and acoustic respiration rate (RRa) (among possibly others). The addition of the acoustic respiration rate can result in the display of the physiological monitoring system 100 outputting a second waveform (e.g., an acoustic respiration waveform).

The board 134 can include a signal processing system. Embodiments of the signal processing system can employ a noise filtering system configured to filter the data obtained during pulse oximetry measurements using red and infrared light, as such data is often contaminated due to motion. Identification and removal of these motion artifacts is often a prerequisite to any signal processing used to obtain blood oxygen saturation, pulse rate, or other physiological data. The signal processing system can provide the desired parameters as outputs for a display. Outputs for display are, for example, blood oxygen saturation, heart rate, and a clean plethysmographic waveform. Complex operations such as noise filtering and signal processing can require specialized processing or significant computational overhead, such that a typical user mobile device can not have sufficient processing power. Accordingly, the processing module 130 can perform signal processing on raw data received from the sensor and can provide physiological parameters as an output to a display and/or storage device.

The connection port 150 includes shell 151, bend relief 152, connector 153, and cap 154. Bend relief 152 is an important feature of a medical cable assembly for both the electrical and mechanical integrity and performance of the second cable 140. The connection port 150 is typically rigid, and the bend relief 152 provides a transition from the stiffness of the connection port 150 to the flexibility of the second cable 140. Preferably, bend relief 152 will prevent mechanical force applied to the exterior of the cable from being transferred to the electrical terminations within the connector, which could lead to failure.

Shell 151 generally encloses connector 153 and can be matable with cap 154 to provide added protection for the connector 153. Connector 153 can be shaped to physically and electrically connect with a specific device. Connection port 150 can be one of many different types of ports. For example, connection port 150 can be a device-specific port such as an iPhone port or another smartphone port, a USB port, an Ethernet port for connection to a wired network, a serial port (e.g., RS232), a video out port which allows projection of the device screen on a larger display, combinations of the same, or the like. Further, the connection port 150 can be equipped with one or more wireless interfaces (such as WiFi, Bluetooth, Zigbee, or the like).

Figure 2:
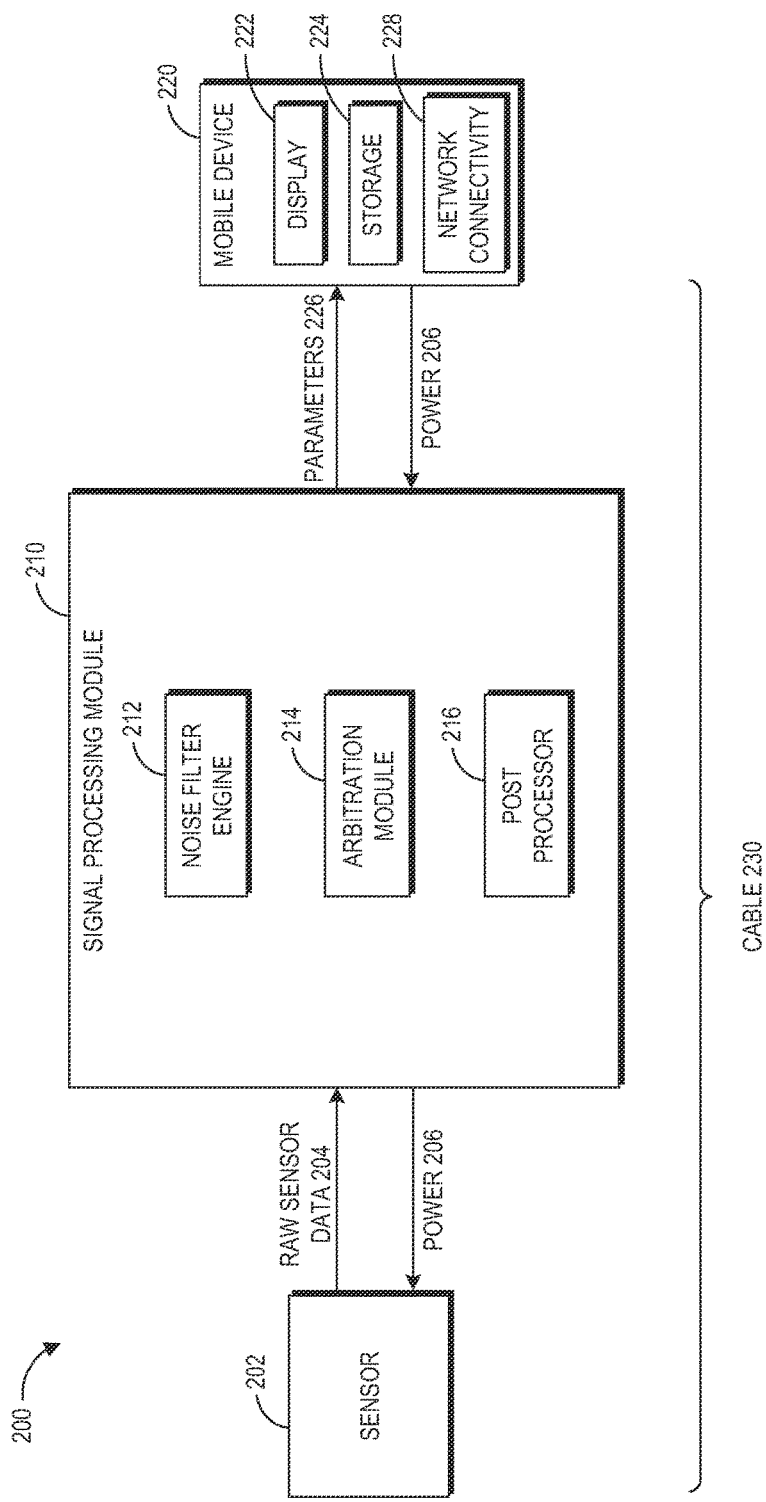
FIG. 2 illustrates a block diagram of an embodiment of a mobile physiological monitoring system.

FIG. 2 illustrates a block diagram of an example physiological monitoring system 200. As illustrated, the system 200 includes a cable 230 and a mobile device 220. The cable 230 includes a sensor 202, which can be any of the physiological sensors described above with respect to FIGS. 1A, 1B, and 1C, and a signal processing module 210. The mobile device 220 can provide power 206 to the signal processing module 210 and the sensor 202. The sensor 210 can transmit raw data 204 to the signal processing module 210, and the signal processing module can convert the raw data 204 into data representing physiological parameters 226 for transmission to the mobile device 220.

The mobile device 220 can be any of the portable computing devices discussed above, such as a smartphone, laptop, tablet, or the like. The mobile device 220 can include a display 222 for display of the parameters, for example in a user interface and/or software application, as discussed in more detail below. The display 222 can include a display screen such as an LED or LCD screen, and can include touch sensitive technologies in combination with the display screen. The mobile device 220 can also include storage 224, which can be configured for storage of parameters 226 and parameter history data and/or software applications for managing the data and sensor 110. In some embodiments, the storage 224 can be physical storage of the device 220, and in some embodiments the storage 224 can be remote storage, such as on a server or servers of a data hosting service. The mobile device 220 can also include a network connectivity feature 228 such as Bluetooth, satellite network capability, mobile communications capability, Wi-Fi, or the like. In some embodiments the mobile device 220 can also include a data transfer port.

The signal processing module 210 can be configured to receive raw sensor data 204 from the sensor 202, and to process the raw data 204 into identifiable parameters 226 for display and/or storage by the mobile device 220. In some embodiments, the mobile device 220 can not have sufficient processing power to handle the conversion of raw data 204 to identifiable parameters 226. For example, in the context of pulse oximetry, the signal processing module 210 can use adaptive filter technology to separate an arterial signal, detected by a pulse oximeter sensor, from the non-arterial noise (e.g. venous blood movement during motion). During routine patient motions (shivering, waving, tapping, etc.), the resulting noise can be quite substantial and can easily overwhelm a conventional ratio based oximetry system. This can provide accurate blood oxygenation measurements even during patient motion, low perfusion, intense ambient light, and electrocautery interference. Accordingly, false alarms can be substantially eliminated without sacrificing true alarms.

The signal processing module 210 can include a noise filter engine 212. In some embodiments, the noise filter engine 212 can perform a discrete saturation transform process to substantially remove noise from the raw sensor data 204. The discrete saturation transform process outputs a maximum power as an $SpO_2$ percentage. For example, the discrete saturation transform process can build a noise reference signal from incoming red and infrared signals of a pulse oximeter sensor, in some embodiments, for each percent $SpO_2$, from 1 to 100 percent. The noise reference signal can be passed through an adaptive filter which can cancel correlated frequencies between the reference signal and the incoming infrared signal. If the frequencies between the two inputs are all similar, the entire signal can be canceled, and a low energy output occurs. If the frequencies between the two inputs are dissimilar, a minimal amount of signal cancels and a high-energy output can be obtained. The energy output from the adaptive filter can be measured and plotted for all possible saturations from 1 to 100 percent, for example in 0.5 percent increments every 0.4 seconds, in some embodiments. During measurements in which the user exhibits no motion, a discrete cosine transfer algorithm can generate one energy output peak, and several output peaks can be generated during motion. Because arterial blood has the highest oxygen saturation, a peak picker process can select the highest saturation peak as the percent $SpO_2$.

In some embodiments, the noise filter engine 212 can employ a plurality of adaptive filter processes in parallel to separate the physiological signal from the noise, and can leverage the unique strengths of each adaptive filter processes to obtain accurate readings through various patient conditions. For example, in one embodiment of pulse oximetry measurements, parallel adaptive filters can include a discrete saturation transform, sinusoidal saturation transform, and fast saturation transform, as well as possibly others. A sinusoidal saturation transform can be a time domain transform that defines a window around a derived pulse rate estimate, subtracts a preselected set of frequencies to find a minima, and can use the minima to determine the location of the maximum power and thus the true pulse rate. A fast saturation transform may include, in some embodiments, a spectral or Fourier transform, a spectral analysis, and identification of physiological parameters through frequency, magnitude, or other aspects of the spectral analysis. In one embodiment, demodulation and decimation of the raw sensor data 204 may occur prior to the fast saturation transform.

The noise filter engine 212 can optionally include an arbitration module 214 in embodiments where multiple calculation engines are used. In some embodiments, the arbitration module 214 may be a confidence-based arbitrator. The arbitration module 214 can include instructions to compare the output of each adaptive filter process in order to generate a final determination of the denoised physiological signal. The arbitration module 214 can also arbitrate physiological measurements based on any number of parameters, for example a highest confidence level or whether a threshold confidence level was reached. Furthermore, the arbitration module 214 can arbitrate based on expected values, previous values, averages or the like. Post processor 216 can apply additional signal conditioning techniques to the output of the arbitration module 214 in order to output parameter data 226 to the mobile device 220.

II. Example Computing Environment

Figure 3:
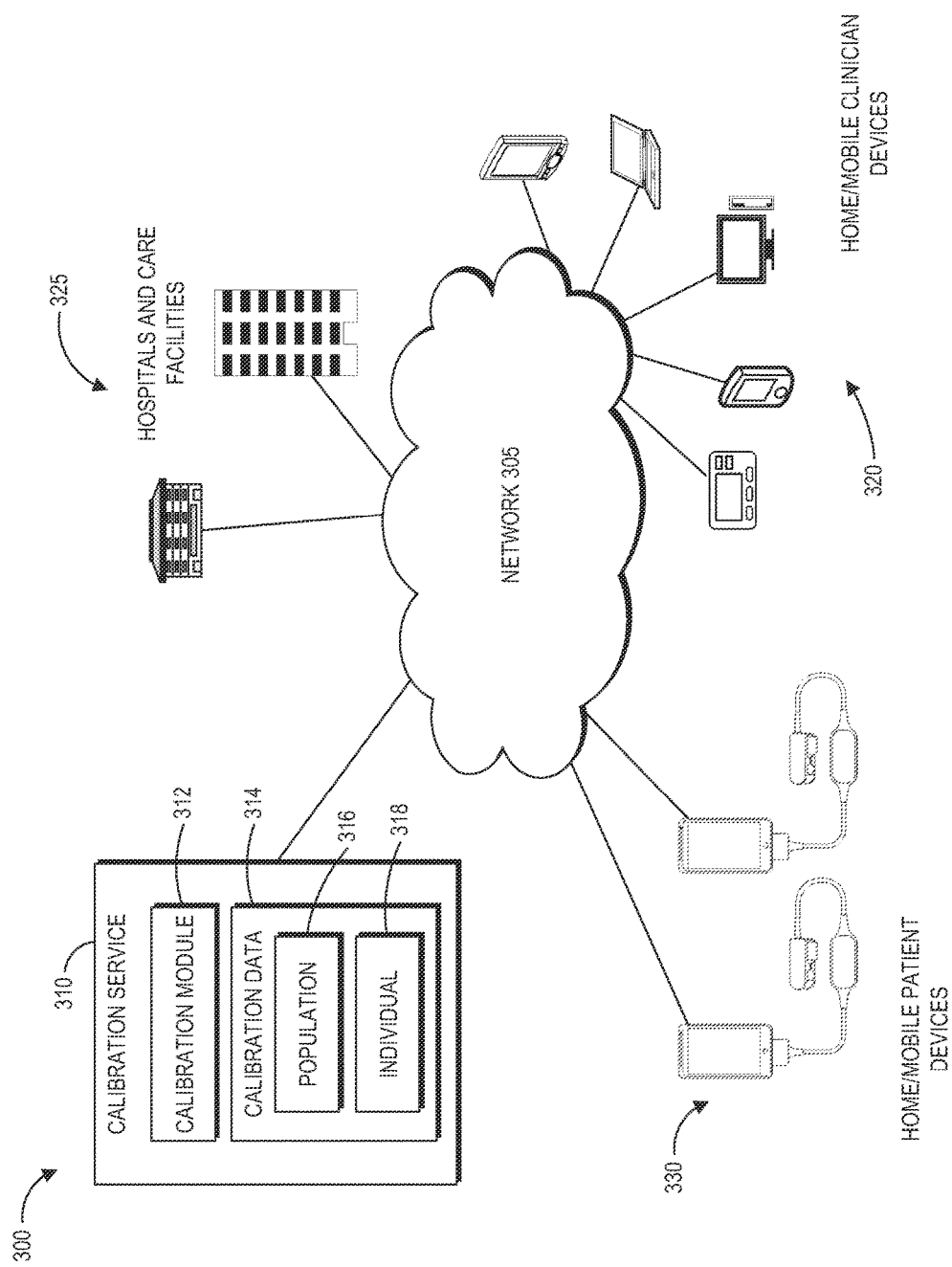
FIG. 3 illustrates an embodiment of a computing environment in which a mobile patient monitoring device can communicate with various computing devices and services over a network.

FIG. 3 illustrates an embodiment of a computing environment 300 in which a mobile patient monitoring device 330 can communicate with various computing devices and services over a network 305. Although various devices and services are illustrated, in some embodiments the mobile patient monitoring device 330 can be configured to communicate with a subset of the illustrated devices and services, and in some embodiments can be configured to communicate with only one of the illustrated devices and services.

In an embodiment, the mobile patient monitoring device 330 can communicate over a network 305 with calibration service 310 over the network 305. The example network 305 shown can be a local area network (LAN), wide area network (WAN), the Internet, an intranet, cellular communications network, satellite communications network, or combinations of the same or the like. The calibration service 310 can accumulate and aggregate received physiological measurement data as calibration data 314 to generate more accurate parameter values. Calibration data for physiological sensors such as pulse oximeters is typically calculated over a patient sample from a clinical study. The clinically generated calibration data can be supplemented, in some embodiments, by the calibration data 314 gathered from physiological sensors 330. Advantageously, gathering measurement data from a number of mobile physiological sensors 330 can expand such a data set significantly and lead to higher accuracies and/or new discoveries regarding parameter measurement. The calibration data 314 can be stored anonymously or in other manners which are compliant with privacy laws regarding medical data. In some embodiments, non-identifying demographic information can advantageously be associated with the calibration data 314.

The calibration service 310 can include a calibration module 312 configured with instructions to calculate a best fit function for the population data 316 within the calibration data 314. The best fit function can be used to generate a calibration curve associating sensor reading values with parameter values. The best fit function can be transmitted to connected patient devices 330 in order to associate sensor readings with more accurate parameter values. Specifically, false positives can be reduced, variances in $SpO_2$ can be detected and filtered, and/or measurement confidence can be evaluated, among other advantages. Calibration data 314 can also include individual data 318, for example individual variations from the expected sensor reading to parameter value relationship defined by the best fit function. Methods of using a single sensor to improve calibration data which can be implemented by the disclosed systems are disclosed in U.S. patent application Ser. No. 13/733,782, titled "AUTOMATED CCHD SCREENING AND DETECTION," filed Jan. 3, 2013, the entirety of which is hereby incorporated by reference.

In an embodiment, the mobile patient monitoring devices 330 can communicate with home/mobile clinician devices 320 over the network 305. Any type of clinician computing device 330 can communicate with mobile patient monitoring device 330 including, for example, laptops, desktops, servers, work stations, tablets, wireless handheld devices such as cell phones, smart phones, personal digital assistants and wireless pagers, combinations of the same or the like. Alternatively or additionally, the mobile patient monitoring devices 330 can communicate with patient databases of hospitals and other care facilities 225 over the network 305. The mobile patient monitoring device 330 can output parameter data, trend data and/or alarms to the home/mobile clinician devices 320 and/or hospitals and other care facilities 225.

III. Example Software Applications

FIGS. 4A-4D illustrate various embodiments of applications for display and management of physiological monitoring data. Such applications can be available for download or installation on a user device from a provider of the physiological sensors described herein, for example from the provider's web site, or through a mobile store application. In an embodiment, a mobile physiological monitoring software application can be initialized when a user connects a sensor cable to their mobile device. The user interface examples illustrated in FIGS. 4A-4D are provided to illustrate and not to limit the capabilities of such applications.

Figure 4A:
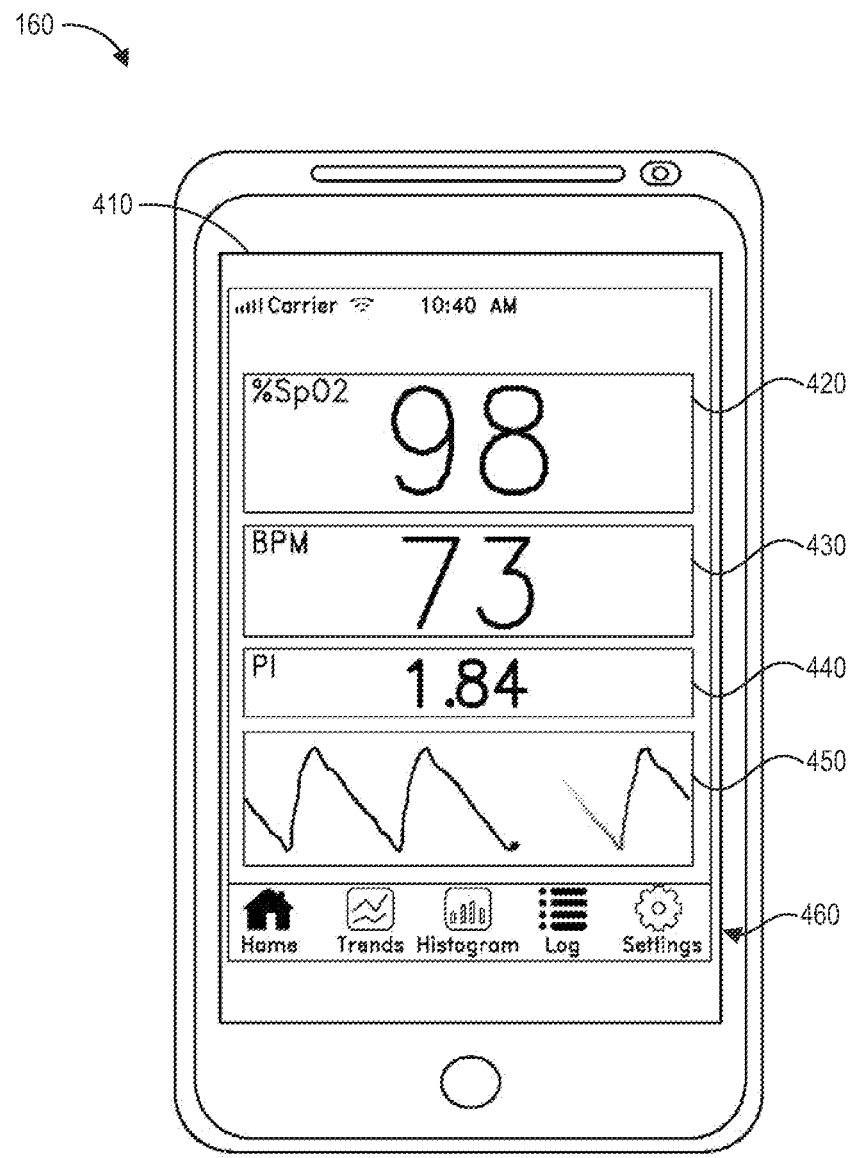

Some embodiments of the software application can be used with the smartphone 160 of FIGS. 1A, 1B, and 1C, though any mobile user device can be used in other embodiments. As illustrated in FIG. 4A, smartphone 160 includes a display 410, which can be used to generate a user interface for the software application. The application can include a plurality of display portions in which a plurality of physiological parameters can be displayed, such as $SpO_2$ display 420, heart rate display 430, perfusion index display 450, or plethysmographic waveform display 450. Any combination of the physiological parameters disclosed herein can be displayed on the smartphone 160. The configuration of these various display portions is meant for illustrative purposes, and one skilled in the art would appreciate that the parameter displays could be rearranged relative to one another, displayed alone, or the user interface could be modified to include other parameter display portions. Another example of a variety of display portions is illustrated in FIG. 4B. Further, although some of the parameter display portions employ numerical representations of the physiological data, some embodiments can employ graphical representations, for example a beating heart can indicate heart rate.

The user interface can also include an options display portion 460 which allows the user to interact with his physiological monitoring data in a variety of ways. For example, the user can choose to view trends in the data, as illustrated in FIG. 4C, or to change the manner in which the data is represented such as by viewing a histogram or other graph. The user can be also able to view the history of his physiological measurement data. In some embodiments, history or trend data can be displayed with a start date and/or time and an end date and/or time, and the user can be able to adjust the window of data displayed. For example, on a touch sensitive interface the user can narrow or expand a window of trend data using a pinch gesture with two fingers. The user can also be able to export a selected amount of trend or history data, such as by electronic mail, through a medical service, or as a spreadsheet, to name a few examples. A settings option can be displayed which would allow the user to modify other aspects of the program, and can also enable the user to set alarms or reminders to take future measurements.

Figure 4D:
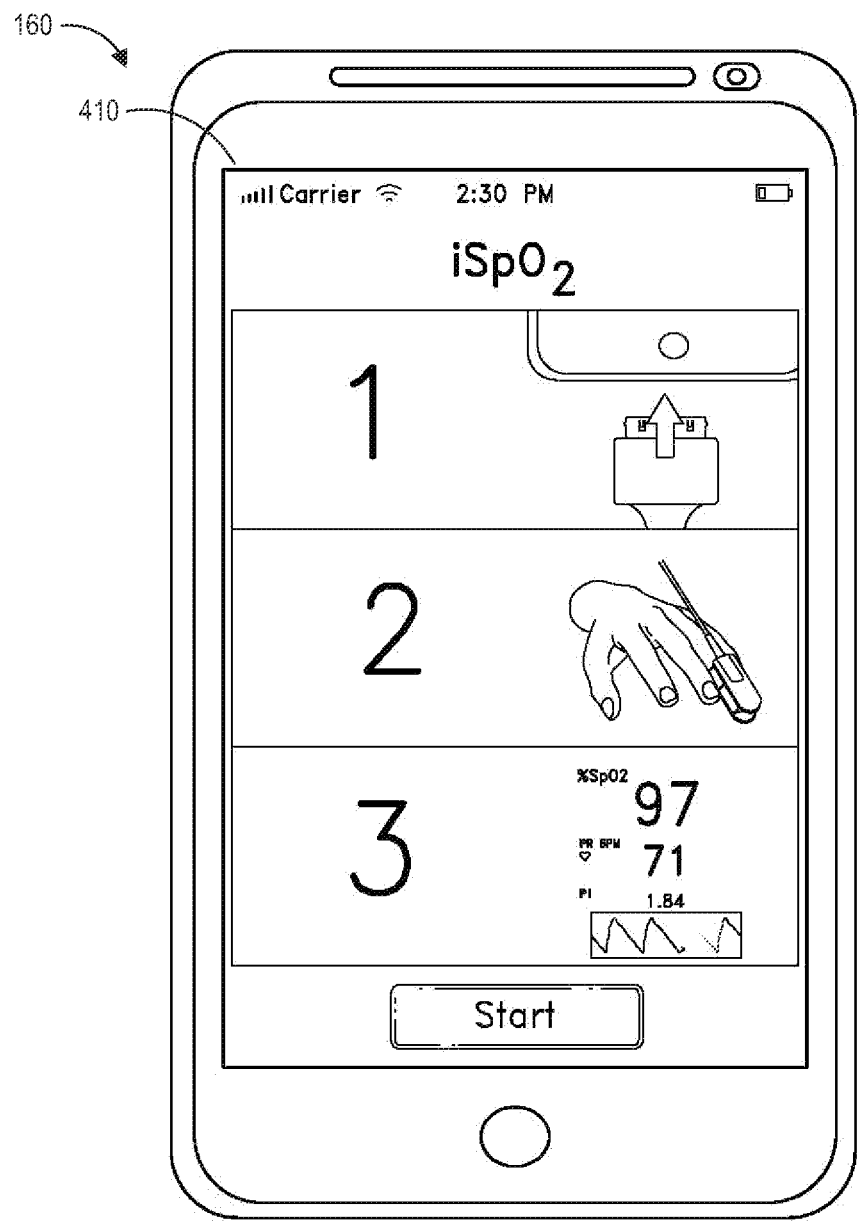

Turning to FIG. 4D, an example instruction user interface is shown which can be presented to a user upon initialization of the application. The instruction interface can include graphical and numbered steps to guide the user through set up of the sensor, and can include a user selectable option to start tracking physiological parameter measurements.

In certain embodiments, the application can be downloadable from a computer network at a cost, by subscription, pay-per-use, or the like. Other embodiments can advantageously incorporated caregiver-specific applications which include reminders for timed measurements or protocols. For example, a caregiver for a pre-surgical patient can desire measurement data for a certain minimum time per minimum period (20 min per every hour) or the like to have sufficient data to make diagnosis or decisions for treatment. A caregiver-specific application can be advantageously programmed to accomplish such a protocol. Moreover, signal quality or confidence indicators such as perfusion index ("PI") or signal IQ ("SIQ") can be used to ensure data meets certain minimum confidence and/or signal-to-noise limitations. Thus, the application can implement the protocol and extend or add measurement intervals to ensure minimum signal quality standards are met. Other caregiver-specific applications can provide animated or textual instructions, links to online information regarding certain monitoring situations, ailments, or other useful patient research.

In an embodiment, data acquired through the application can be uploaded to caregiver or device provider systems to increase the population data and used to improve signal processing. In a preferred embodiment, issues of privacy and compliance with governmental regulations are strictly enforced through the application logic. In some embodiments, non-identifying demographic information can advantageously be associated with such data. Moreover, password and/or additional authentication requirements can be required to access stored data in the application, such as, for example, fingerprint technologies, facial recognition technologies employing the smartphone's camera, voice recognition technologies employing the smartphone's audio transducer, or the like can further assist in meeting privacy concerns.

IV. Overview of Compatible Sensor Embodiments

Figure 5A:
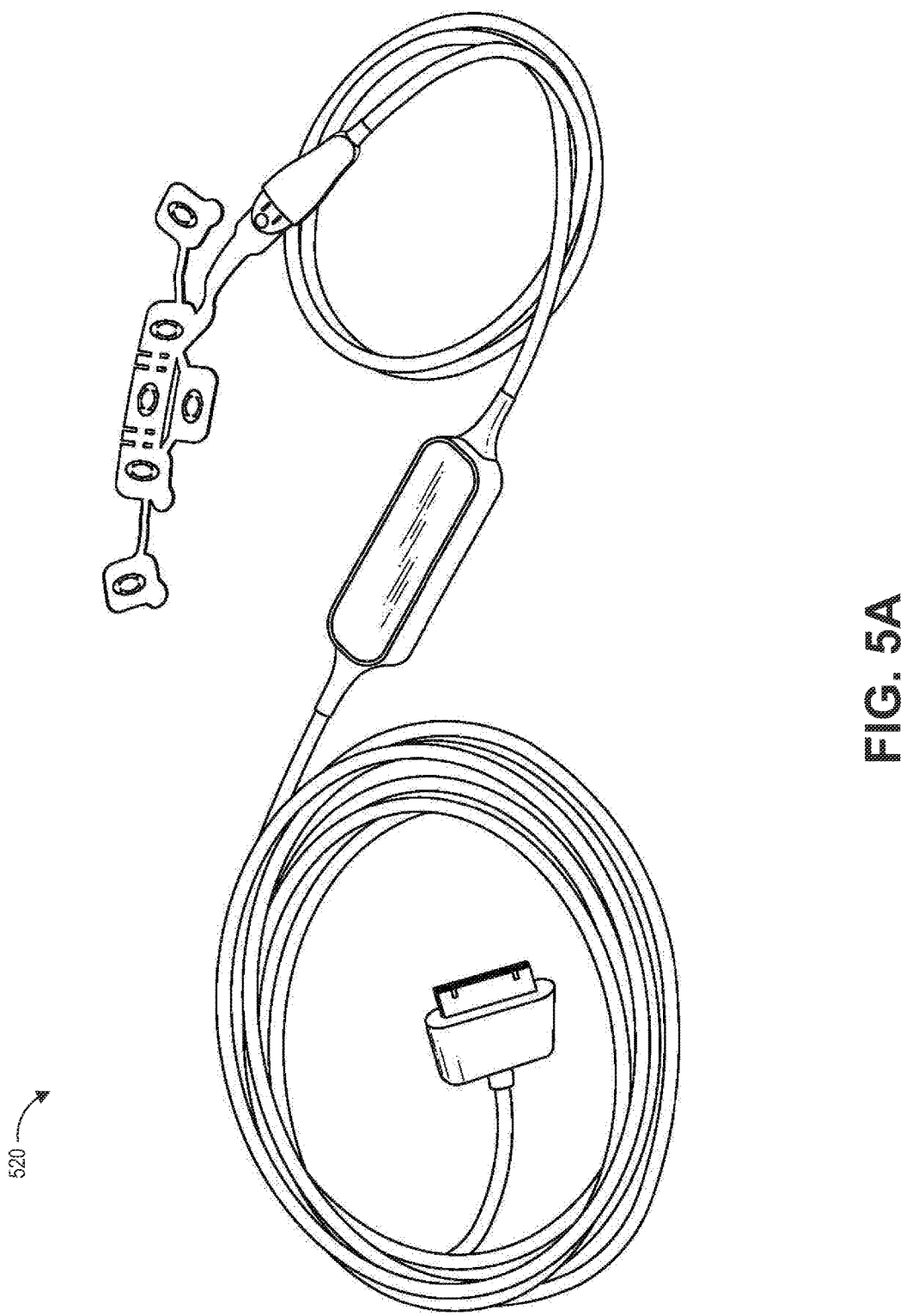

As illustrated in FIG. 5A, a physiological sensor 520 can be an electroencephalograph ("EEG") configured for measurement of electrical activity along the scalp. Such mobile EEG systems can be used, for example, in detecting and monitoring epileptic activity. EEG systems can also be used for diagnosis and management of sleep disorders or for studies of sleep. Electroencephalography is used extensively in neuroscience, cognitive science, cognitive psychology, neurolinguistics and psychophysiological research. In many of these contexts, a sensor 520 compatible with a common mobile computing device of a user would provide advantages such as convenience and affordability. In some embodiments, the sensor 520 can be SEDLine®, available from Masimo. SEDLine® brain function monitoring can use four channels of information, in some embodiments, to monitor both sides of the brain's electrical activity.

Turning to FIG. 5B, a capnometer or capnograph 530 can be configured for mobile physiological parameter measurement. Such sensors 530 can be designed for the measurement of $CO_2$, $N_2O$, and anesthetic agents, among others. Capnography can be useful for metabolic measurements and nutritional assessment, and accordingly a mobile sensor 530 can provide increased accessibility for such uses.

An acoustic respiratory monitor 540, as shown in FIG. 5C, can also be configured for mobile physiological parameter measurement. An acoustic respiratory monitor 540 can measure respiration rate using an adhesive sensor with an integrated acoustic transducer that can be comfortably applied to the patient's neck. Continuous monitoring of respiration rate can be important for post-surgical patients receiving patient-controlled analgesia for pain management, as the sedation can induce respiratory depression and place patients at considerable risk of serious injury or death. Accordingly, a mobile respiratory monitor 540 can be desirable for convenient and continuous monitoring of such patients, among other reasons.

V. Overview of Example Mobile Physiological Monitoring Processes

Figure 6:
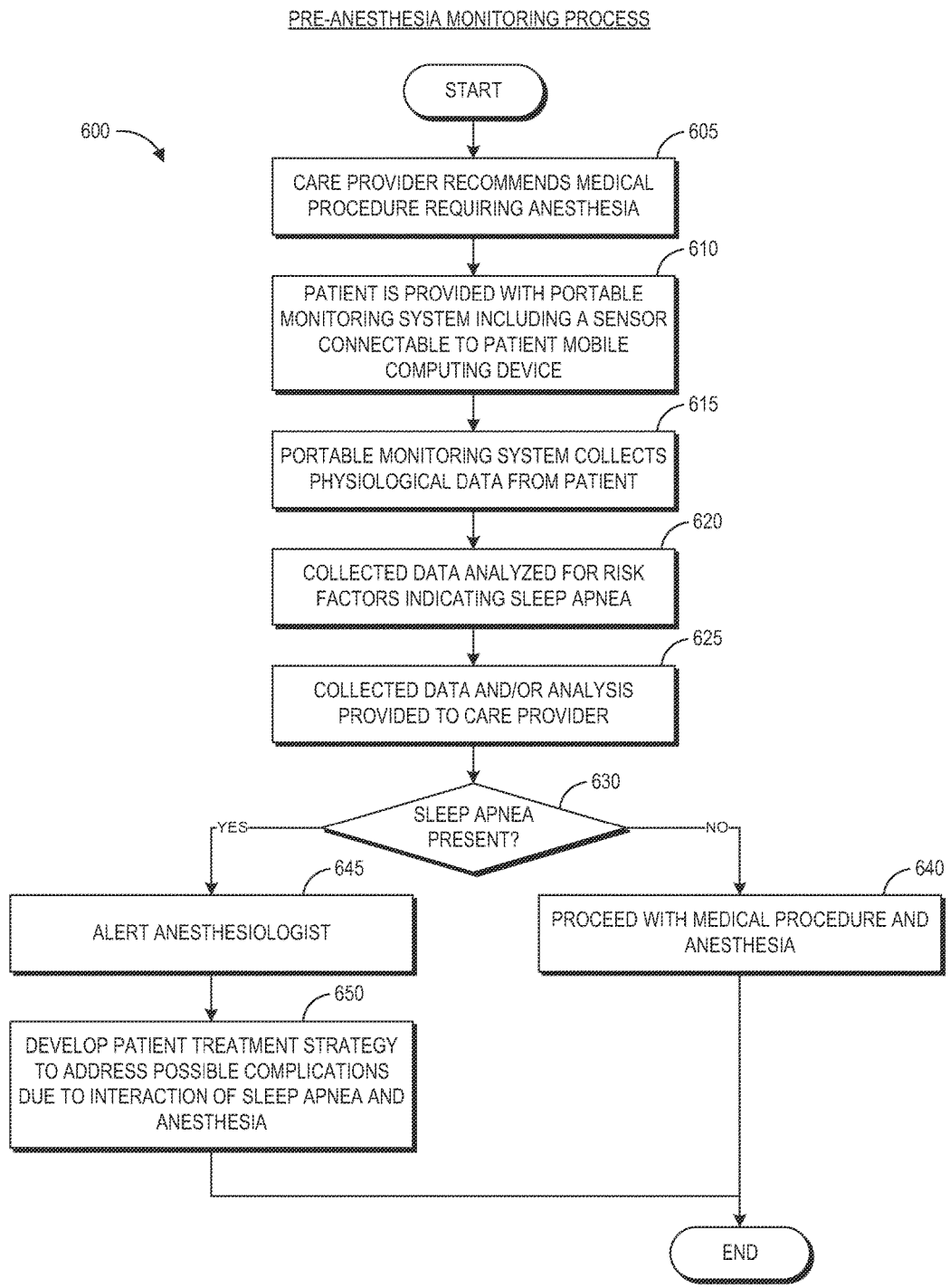
FIG. 6 illustrates an embodiment of a pre-anesthesia monitoring process.

FIG. 6 illustrates an embodiment of a pre-anesthesia monitoring process 600. The process can be implemented by the physiological monitoring system 100 of FIGS. 1A, 1B, and 1C, in some embodiments.

The process 600 can begin at block 605 in which a care provider recommends a medical procedure requiring anesthesia for a patient. Certain medical conditions can present safety concerns for the patient during anesthesia, so at block 610 the patient can be provided with a portable monitoring system including a sensor connectable to one of the patient's personal mobile computing devices. In some embodiments the patient can be provided with multiple sensors and/or a software application for collection and management of physiological data.

At block 615, the portable monitoring system can collect and store physiological data from the patient. Optionally, at block 620, the collected data is analyzed for risk factors indicating a medical condition with implications for anesthesia, such as obstructive sleep apnea. At block 625, the collected data and/or analysis of the data is provided to the patient's physician or another care provider. In some embodiments, a physician can conduct the analysis after receiving the patient's data.

At decision block 630, a determination is made regarding whether the data analysis indicates that sleep apnea or another medical condition impacting the safety of anesthesia is present. If such a condition is present in the data, then the process 600 moves to block 645 in which the anesthesiologist is alerted. At step 650, a patient treatment strategy is developed that addresses the possible complications of the patient undergoing anesthesia with the detected condition. If no safety-impairing medical condition is present in the data, then the process 600 moves to block 640 in which the patient's physician can elect to proceed with the recommended medical procedure and anesthesia.

Figure 7:
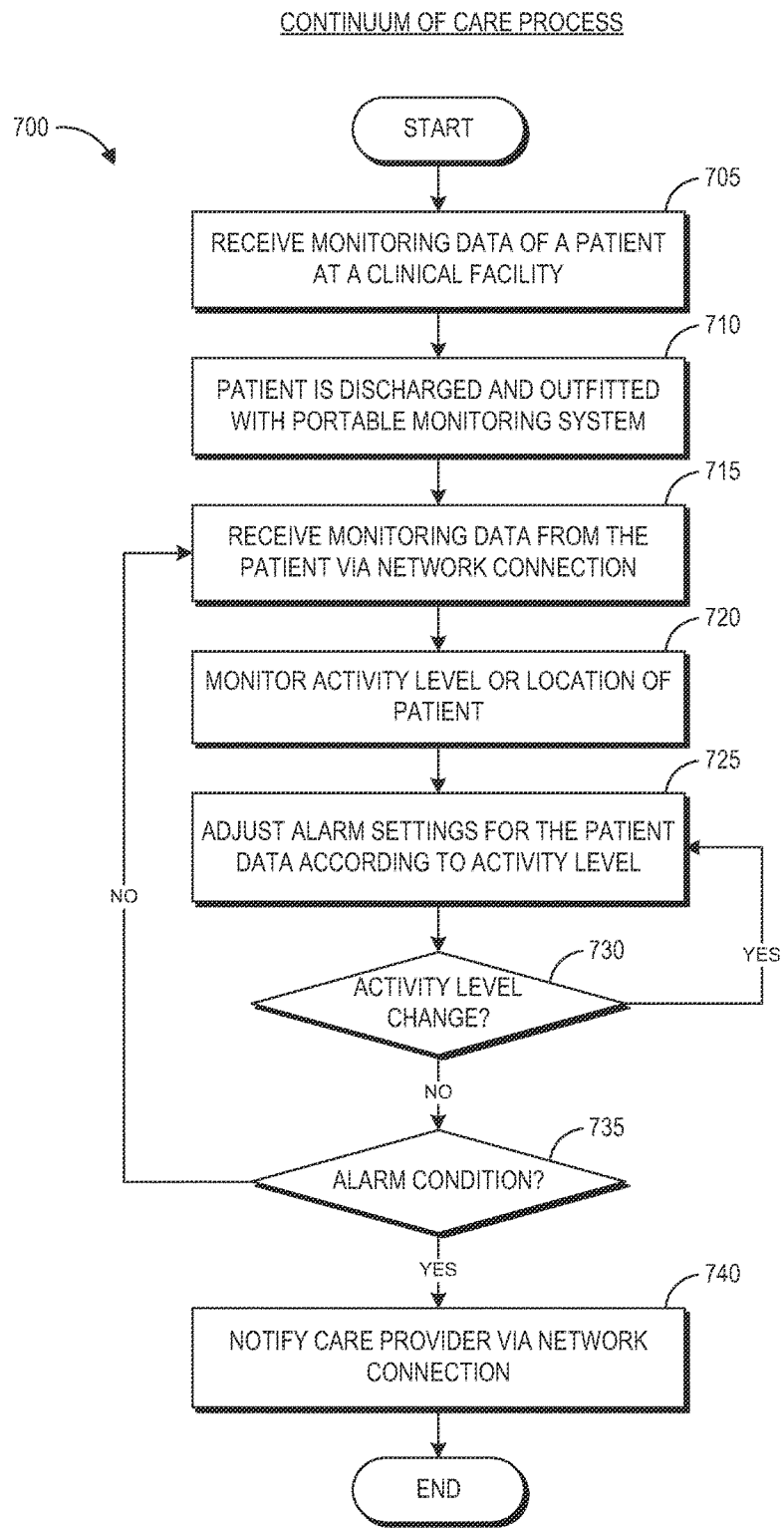
FIG. 7 illustrates an embodiment of a continuum of care process.

FIG. 7 illustrates an embodiment of a continuum of care process 700. The process 700 can be implemented, in some embodiments, by the computing environment 300 of FIG. 3. In an embodiment, the process 600 can be implemented at least in part by the network 305 to facilitate continued patient monitoring when a patient leaves a hospital or other facility.

At block 705, monitoring data of a patient is received at a clinical facility, for example by a networked medical service which can receive and store patient monitoring data, among other features. Once the patient is discharged, at block 710 the patient can be outfitted with a portable monitoring system. The portable monitoring system can monitor the same parameters as a device used to monitor the patient in the clinical facility. In addition, the portable monitoring system may, for instance, be any of the sensors and processing cable components, or variations thereof, described herein.

When a patient is discharged, there is a typically a period of time where the patient is not being monitored once the patient leaves the facility. However, the continuum of care process 700 employing mobile physiological sensors can facilitate continued monitoring of the patient, for example during travel between the facility and the patient's residence or when the patient arrives at home, by receiving monitoring data from the patient via a cellular or satellite network at block 715. An activity level of the patient, for example resting or walking, can be monitored at block 620 in order to set the appropriate thresholds for determining when physiological parameters indicating an alarm condition are occurring at block 725. The patient's activity level can be monitored by the device, in some embodiments, or can be input by the patient or a care giver.

Periodically, the mobile physiological sensor system can recheck the patient's activity level at block 730 to determine whether the activity level has changed. If the patient's activity level has changed, then the process 700 loops back to block 725 to adjust alarm settings for the patient's physiological data based on the activity level. If the patient's activity level has not changed, then the process 700 can move to block 735 in which it is determined whether an alarm condition is occurring based on the patient's physiological parameters and the alarm settings. A software application installed on the patient's mobile device can be configured to detect the alarm condition. If an alarm condition is not occurring, then the process 700 loops back to block 715 in which the mobile physiological sensor continues to perform physiological measurements and transmit the measurements to the mobile device through a signal conditioning processor. If an alarm condition is detected at block 735, then the patient's mobile device can pass a notification to a care provider via a network connection. Accordingly, the mobile physiological sensor system can facilitate a continuum of care for a patient and continuous monitoring even when a patient has left a clinical facility.

Figure 8:
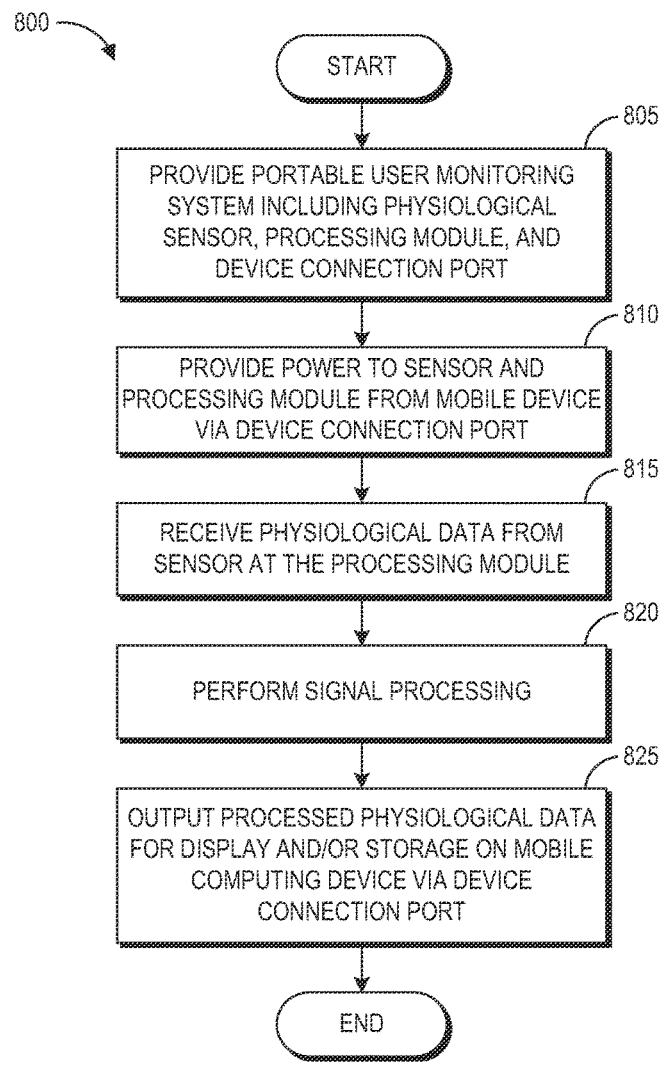
FIG. 8 illustrates an embodiment of a mobile physiological data monitoring process.

FIG. 8 illustrates an embodiment of a mobile physiological data monitoring process 800. The process can be implemented, in some embodiments, by the physiological monitoring system 100 of FIGS. 1A, 1B, and 1C, or the physiological monitoring system 200 of FIG. 2.

At block 805, a portable user monitoring system is provided including physiological sensor, processing module, and device connection port. The physiological sensor can be any of the sensor examples discussed herein. The processing module can be the processing module 130 described in FIGS. 1A, 1B, and 1C or the signal processing module 210 of FIG. 2. The processing module can implement Masimo SET technology, in some embodiments. The device connection port can be configured for use with a standard personal computing device, such as a smartphone, and can be connected to the processing module physically via a cable or wirelessly.

At block 810, the user's mobile computing device, while connected to the portable patient monitoring system, provides power to the sensor and processing module. Accordingly, the sensor and processing module can be configured in some embodiments so as to draw only minimal power from the mobile computing device, as such devices are typically powered by batteries.

At block 815, the processing module receives raw physiological sensor data from the sensor. The processing module performs signal conditioning on the raw data at block 820, for example any of the signal conditioning techniques described herein, to remove noise from the raw data and obtain physiological parameter data. At block 825, the processing module outputs the physiological parameter data to the user's mobile computing device for display and/or storage on the device. Accordingly, a user can conveniently conduct physiological measurements and be presented with physiological data on their mobile device in a wide variety of contexts.

Figure 9:
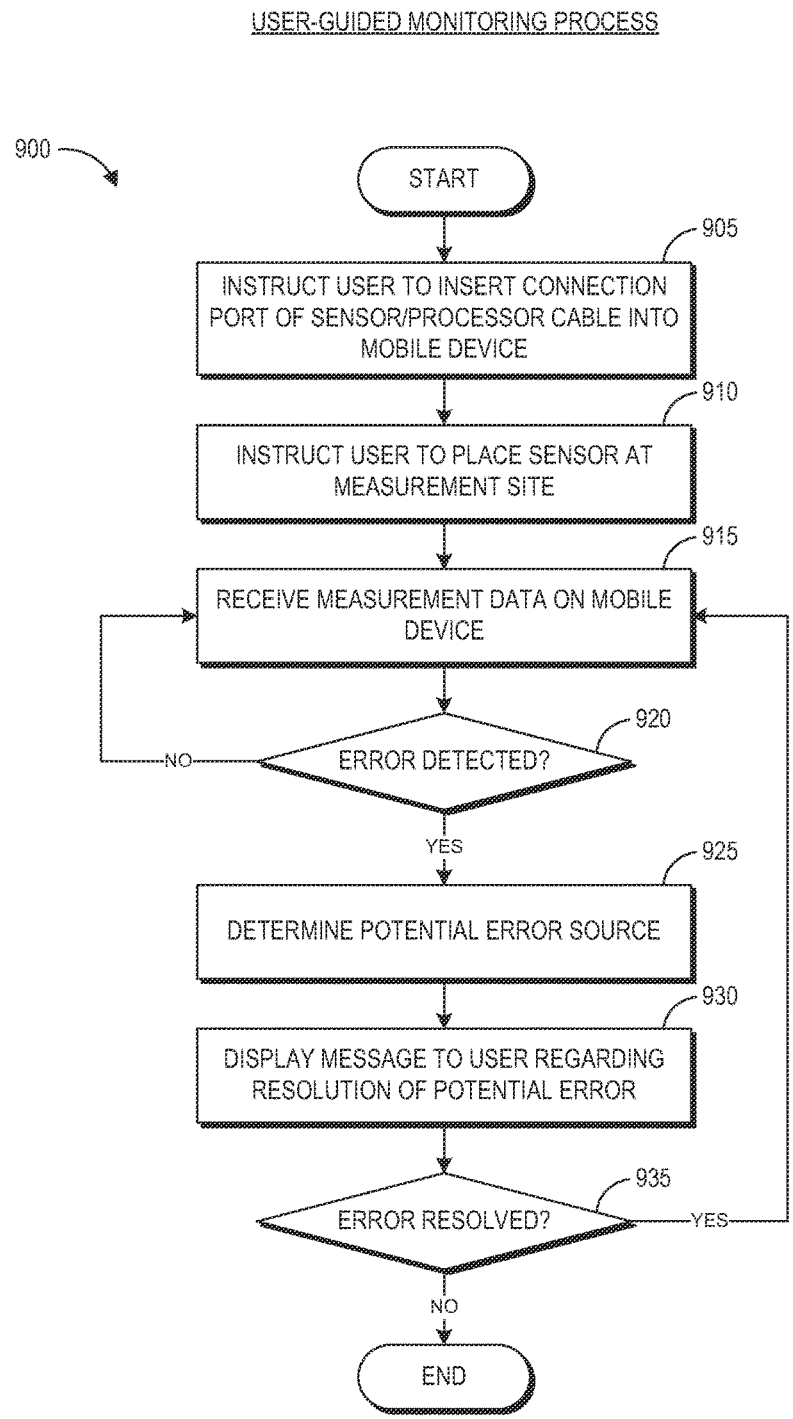
FIG. 9 illustrates an embodiment of a user-guided monitoring process.

FIG. 9 illustrates an embodiment of a user-guided monitoring process 900, which can be carried out by a user on their personal computing device without the need for physician or caregiver aid. The process 900 can be carried out by a mobile physiological monitoring application, as discussed above, in conjunction with a mobile physiological sensor. The physiological sensor can be any of the sensor examples discussed herein.

At block 905, the user is instructed to insert the connection port of a cable including a physiological sensor and a processor into a corresponding port on their mobile computing device, and at block 910 the user is instructed to place the sensor at a measurement site. In some embodiments, these blocks can be implemented by an instruction user interface such as is depicted in FIG. 4D and discussed above.

At block 915, the mobile device receives measurement data, which can be raw sensor data that has been processed by a processing module prior to being sent to the mobile device. At block 920, the mobile physiological monitoring application can determine based on the measurement data whether an error is occurring. If it is determined that an error is not occurring, then the mobile device can continue to receive measurement data at block 915. If it is determined that an error is occurring, then the mobile physiological monitoring application can determine a potential or likely error source at block 925.

Based on the determined error source, the mobile physiological monitoring application may, at block 930, display a message to aid the user to aid in resolution of the error. Example messages include "Ensure cable is connected," "Sensor not working." "Place sensor on properly," "Searching for pulse," "Interference detected, see manual," "Low perfusion, see manual," "Too much surrounding light," "Low signal quality, see manual," and "Connecting, please wait," among others. In some embodiments an audible or visual indication can also be provided to alert the user to the presence of the error. At block 935, the mobile physiological monitoring application can determine whether the user has resolved the error. The mobile physiological monitoring application can repeat this action at predetermined intervals until the error is resolved or the application is terminated by the user, in some embodiments. In other embodiments, the mobile physiological monitoring application can determine whether the error has been resolved based on a change in received measurement data values. If, after a predetermined threshold of time, the error is not resolved, then the process 900 ends. If the error is resolved, the process 900 loops back to block 915, and the mobile device can continue to receive measurement data.

Figure 10:
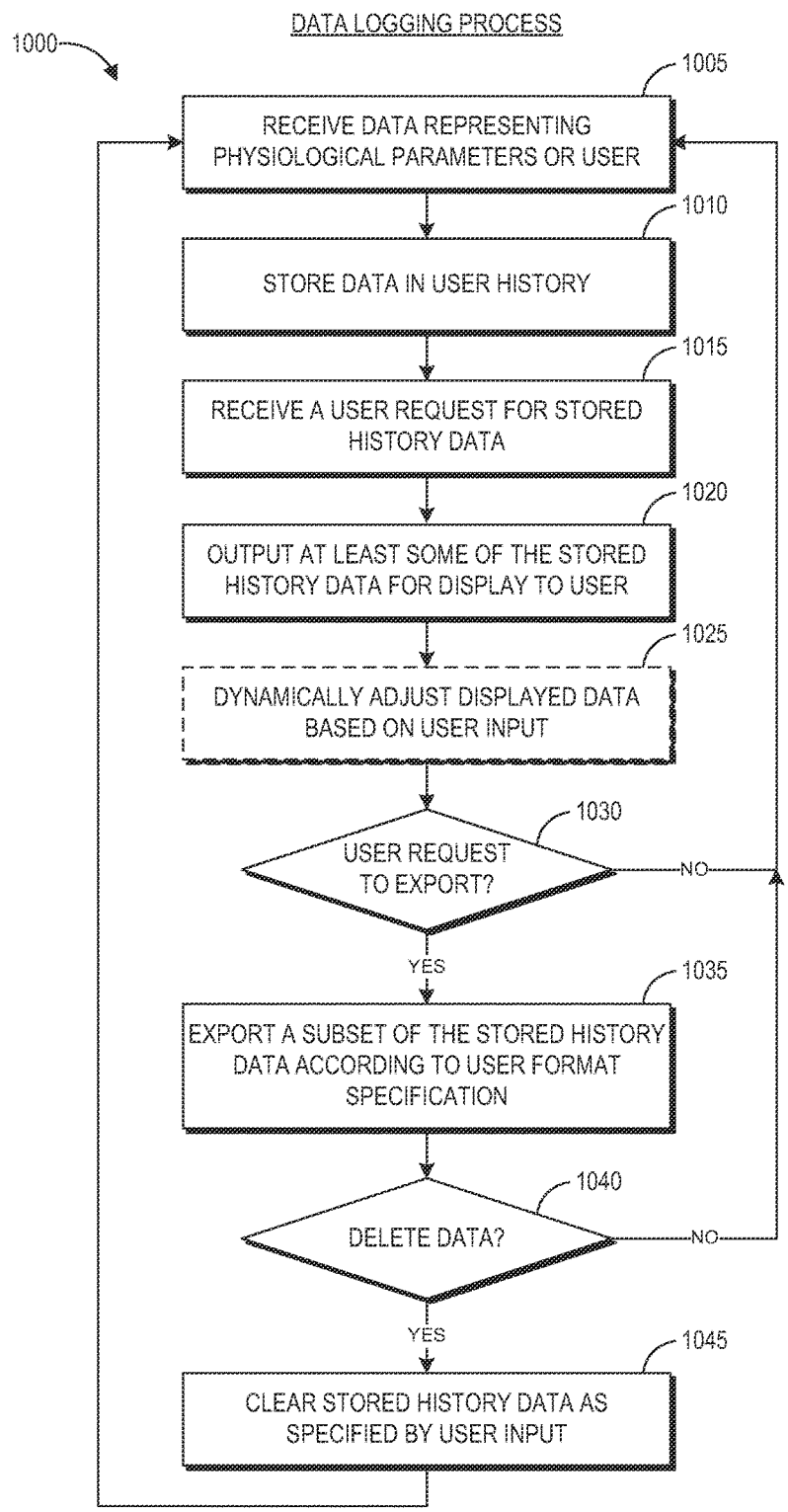
FIG. 10 illustrates an embodiment of a data-logging process.

FIG. 10 illustrates an embodiment of a data-logging process 1000. The data-logging process 1000 can run continuously or periodically during operation of a mobile physiological monitoring application, as discussed above.

At block 1005, the mobile physiological monitoring application can receive measurement data, which can be raw sensor data that has been processed by a processing module prior to being sent to a mobile device. This data is stored, at block 101, in a user history, for example in storage of the mobile device or in a networked data storage service. At block 1015, the mobile physiological monitoring application determines that a user has requested to be presented with history data, and accordingly outputs at least some of the stored data for display to the user at block 1020. In some embodiments, the user can specify a desired range of stored history data when making the request. In other embodiments, the device can output a predetermined range of the history data, for example based on a recent time window of the data or patterns in the data.

At block 1025, the mobile physiological monitoring application can dynamically adjust the amount of displayed data based on user input. This step can be optional based on whether a user provides input regarding adjusting the data. In some embodiments, the user can be able to specify particular physiological parameters to add or remove from the display. In an embodiment implemented on a touch-sensitive display, a user can use a two-finger pinching gesture to change the range of the time window of the data, or can use a swiping motion to move forwards or backwards through the data. Such adjustments can be implemented using other user interface elements on non-touch sensitive displays. A user can also be able to select from a variety of possible representations of the data, such as a chart, graph, plot, or other graphical representation as well as numerical representations such as spreadsheets, in some embodiments.

At block 1030, the mobile physiological monitoring application can receive a user request to export the stored history data. If no such request is received, then the mobile physiological monitoring application can loop back to block 1005 and continue to receive physiological measurement data. If the user requests to export the data, then at block 1035 the mobile physiological monitoring application can export a subset of the stored history data according to user format specification. For example, the user can specify a time and/or date range of data to export, can select a format (such as a spreadsheet or a graph), and can select an exporting means such as email or direct transmission to a physician or networked medical service.

At block 1040, the user can be presented with an option to delete the stored history data. In some embodiments, the user can be asked whether to delete data that has been exported. If the user does not want to delete the data, then the mobile physiological monitoring application can loop back to block 1005 and continue to receive physiological measurement data. If the user requests to delete the data, then the mobile physiological monitoring application can clear stored history data according to user instructions, and can then loop back to block 1005 and continue to receive physiological measurement data.

VI. Terminology

Although many of the examples discussed herein are in the context of pulse oximetry, this is for illustrative purposes only. The sensors, signal conditioning techniques, and mobile applications discussed herein can be adapted for other physiological parameters or for multiple physiological parameters.

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor can also include primarily analog components. For example, any of the signal processing algorithms described herein can be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A physiological monitoring system comprising:
    a physiological sensor configured to monitor one or more physiological parameters of a patient;
    a mobile computing device comprising a display;
    a cable including:
        a processing board configured to establish an electrical signal connection between the physiological sensor and the mobile computing device, wherein the processing board is further configured to receive raw data representing the monitored one or more physiological parameters and to perform signal processing to provide filtered parameter data to the mobile computing device,
        a first portion of the cable coupled between the physiological sensor and the processing board, the first portion of the cable extending a first distance mechanically isolating the processing board from the physiological sensor, and
        a second portion of the cable coupled between the processing board and the mobile computing device, the second portion of the cable extending a second distance, wherein the second distance is smaller than the first distance; and
    an enclosure comprising:
        a body portion surrounding the processing board,
        a first bend relief on a first side of the body portion, and
        a second bend relief on a second side of the body portion, the first portion of the cable coupled between the physiological sensor and the processing board through the first bend relief and the second portion of the cable coupled between the processing board and the mobile computing device through the second bend relief.

2. The physiological monitoring system of claim 1, wherein the processing board is coupled to a port using a second portion of the cable, wherein the port is connectable to the mobile computing device.

3. The physiological monitoring system of claim 1, wherein the processing board comprises a digital processing board and an analog processing board.

4. The physiological monitoring system of claim 1, wherein the processing board is in communication with an information element.

5. The physiological monitoring system of claim 1, wherein the mobile computing device provides a power signal to the processing board and the physiological sensor.

6. The physiological monitoring system of claim 1, wherein the mobile computing device presents the filtered parameter data to a user on the display.

7. The physiological monitoring system of claim 1, wherein the mobile computing device further comprises storage configured to store the filtered parameter data.

8. The physiological monitoring system of claim 1, wherein the mobile computing device is configured to transmit, via a network connection, the filtered parameter data to at least one of a calibration service, a physician computing device, or a medical facility patient database.

9. The physiological monitoring system of claim 1, wherein the physiological sensor comprises one or more of a pulse oximeter, capnometer, capnograph, acoustic respiratory sensor, electroencephalograph, electrocardiograph, or temperature sensor.

10. A computer-implemented method of mobile physiological monitoring, the method comprising:
   providing a portable physiological monitoring system comprising:
      a physiological sensor configured to monitor one or more physiological parameters of a patient,
      a cable including:
         a processing board configured to establish an electrical signal connection between the sensor and a mobile computing device,
         a first portion of the cable coupled between the physiological sensor and the processing board, the first portion of the cable extending a first distance mechanically isolating the processing board from the physiological sensor, and
         a second portion of the cable coupled between the processing board and the mobile computing device, the second portion of the cable extending a second distance, wherein the second distance is smaller than the first distance, and
      an enclosure comprising:
         a body portion surrounding the processing board,
         a first bend relief on a first side of the body portion, and
         a second bend relief on a second side of the body portion, the first portion of the cable coupled between the physiological sensor and the processing board through the first bend relief and the second portion of the cable coupled between the processing board and the mobile computing device through the second bend relief;
   generating raw data representing the monitored one or more physiological parameters using the physiological sensor;
   receiving the raw data at the processing board via the first portion of the cable;
   performing signal processing on the raw data using the processing board, wherein the signal processing generates filtered parameter data; and
   transmitting the filtered parameter data via the second portion of the cable to the mobile computing device.

11. The computer-implemented method of claim 10, wherein the signal processing comprises:
   determining a noise signal present in the raw data;
   filtering the raw data to remove the noise signal; and
   outputting the filtered raw data as filtered parameter data.

12. The computer-implemented method of claim 10, wherein the filtered parameter data comprises one or more of oxygen saturation, pulse rate, perfusion index, signal quality, oxygen content, carboxyhemoglobin, methemoglobin, and acoustic respiration rate.

13. The computer-implemented method of claim 10, wherein transmitting the filtered parameter data to the mobile computing device comprises transmitting the filtered parameter data through the cable and a connection port to the mobile computing device.

14. The computer-implemented method of claim 10, wherein transmitting the filtered parameter data to the mobile computing device comprises transmitting the filtered parameter data through the cable to a wireless communication module, wherein the filtered parameter data is transmitted wirelessly to the mobile computing device from the wireless communication module.

15. The computer-implemented method of claim 10, further comprising providing a mobile monitoring application configured to track and display the filtered parameter data.

16. The computer-implemented method of claim 15, wherein the mobile monitoring application is further configured to output stored history data representing filtered parameter data monitored over a period of time.

17. The computer-implemented method of claim 16, wherein outputting stored history data comprises presenting the stored history data to a user on a display of the mobile computing device.

18. The computer-implemented method of claim 16, wherein outputting stored history data comprises exporting the stored history data to another computing device.

19. The computer-implemented method of claim 10, further comprising:
   connecting to a network using the mobile computing device; and
   transmitting the filtered parameter data over the network.

20. The computer-implemented method of claim 19, wherein the filtered parameter data is transmitted over the network to a calibration service, the method further comprising incorporating the filtered parameter data into a calibration data set.

21. The computer-implemented method of claim 20, further comprising using the calibration data set to generate a calibration curve.

* * * * *